(12) United States Patent
Busiashvili

(10) Patent No.: US 6,559,180 B2
(45) Date of Patent: May 6, 2003

(54) NITROGLYCERIN-MENTHOL POTENTIATION FOR TREATMENT OF ANGINA

(76) Inventor: Yuri Busiashvili, 16887 Calle De Sarah, Pacific Palisades, CA (US) 90272

( * ) Notice: Subject to any disclaimer, the term of this patent is extended or adjusted under 35 U.S.C. 154(b) by 0 days.

(21) Appl. No.: 10/104,132

(22) Filed: Mar. 21, 2002

(65) Prior Publication Data

US 2002/0193435 A1 Dec. 19, 2002

Related U.S. Application Data

(60) Provisional application No. 60/279,154, filed on Mar. 27, 2001.

(51) Int. Cl.[7] ........................ A61K 31/21; A61K 31/045
(52) U.S. Cl. ....................................... 514/509; 514/729
(58) Field of Search ................................. 514/509, 729

(56) References Cited

U.S. PATENT DOCUMENTS

| 4,671,953 A | 6/1987 | Stanley et al. .............. 424/440 |
| 5,770,220 A | 6/1998 | Meconi et al. ............... 424/448 |
| 5,855,908 A | 1/1999 | Stanley et al. .............. 424/440 |
| 6,210,699 B1 | 4/2001 | Acharya et al. ............. 424/435 |
| 6,316,029 B1 | 11/2001 | Jain et al. .................... 424/484 |

OTHER PUBLICATIONS

"Nitrolingual Pumpsray" pamphlet by First Horizon Pharmaceutical Corporation. Pertinent section is under "DESCRIPTION" heading. (Aug. 1999).

Primary Examiner—Ray Henley
(74) Attorney, Agent, or Firm—Ralph D. Chabot

(57) ABSTRACT

The strength of a nitroglycerin dosage to be administered to patients suffering from angina can be reduced when a portion of the dosage is replaced with menthol containing substances (MCS). MCS and specifically 1% Menthol has been found to potentate the effect of nitroglycerin. Accordingly, MCS can be used as a substitute for a portion of the nitroglycerin dosage administered to a patient. Side-effects common to nitroglycerin usage such as headache and fainting are significantly reduced when a nitroglycerin/MCS solution is used which has 50% of the nitroglycerin dosage per spray commonly used without sacrificing treatment effectiveness.

5 Claims, No Drawings

NITROGLYCERIN-MENTHOL POTENTIATION FOR TREATMENT OF ANGINA

PRIORITY CLAIM

This application claims the priority of U.S. Provisional Application bearing serial No. 60/279,154 filed on Mar. 27, 2001.

TECHNICAL FIELD

This invention pertains to cardiac medication and specifically to the treatment of angina with a mixture of nitroglycerin (NTG) and menthol containing substances (MCS).

BACKGROUND OF THE INVENTION

Nitroglycerin spray is widely used in patients with coronary artery disease and angina.

Nitroglycerin (NTG) is the most common medication taken for quickly alleviating the pain experienced by someone having an angina attack. The principal pharmacological action of NTG is relaxation of the vascular smooth muscle, producing a vasodilatory effect on both peripheral arteries and veins with more prominent effects on the latter.

NTG, taken sublingually, is very effective; anginal pain usually subsides within minutes. NTG also improves exercise tolerance in patients with exertional angina when used prophylactically. The beneficial effect of NTG is dose related.

NTG is commonly supplied in tablet or liquid form for sublingual delivery. Typically, in liquid form, a pump spray applicator is used and is set to deliver 400 mcg NTG per single spray dosage. It is known in the prior art to add peppermint oil as an inactive ingredient to NTG in the liquid form for sublingual delivery. A commonly used product is manufactured and sold under the US Registered trademark "NITROLINGUAL"® Pumpspray by First Horizon Pharmaceutical Corporation, Roswell, Ga.

The most common side effects associated with NTG medication are headache and syncope. These undesirable side effects are dose related but the effects can vary from patient to patient. For some patients, the side effects can be so intense that they will refuse to take the NTG medication.

SUMMARY OF THE INVENTION

It has been discovered that the use of menthol containing substances (MCS), when used in conjunction with NTG can potentiate the effect of NTG when it is administered to a patient sublingually. Accordingly, MCS permits the usage of a lower minimal effective NTG dosage. In other words, a mixture of MCS with a less than the 400 mcg standard dosage of NTG will provide the same effect as a standard 400 mcg dosage of NTG.

As used in this specification, MCS is used to collectively refer to substances from which Menthol is derived. Substances which are considered to be MCS include peppermint oils, (Ex Mentha Piperita and Ex Mentha Arvensis), peppermint flavor, spearmint oil, or synthetically produced Menthol.

One advantage of combining a reduced amount of NTG with MCS is that the amount of NTG contained in each spray dosage is less while still providing the same level of anginal pain relief but without the patient having to experience the typical dosage related side effects, specifically, headache and fainting he/she would otherwise suffer. A second advantage for using a NTG/MCS combination is the reduced dosage cost since less NTG is required.

By way of example, an approximate 1% Menthol solution can be prepared and mixed in a 50/50 volumetric proportion with NTG solution. The resulting anti-anginal medication can be used for sublingual delivery by aerosol or pump spray. For example, only 200 mcg NTG is used rather than the typical 400 mcg NTG dosage. The NTG anti-anginal effect obtained is as effective as if double the dosage of NTG was used, i.e. 400 mcg NTG; but the dose related side effects are reduced dramatically.

A solution containing 50% vol. standard NTG NITROLINGUAL® Pumpspray (400 mcg/spray) and 50% vol. 1% Menthol was tested. The solution was indicative of the benefit available to a patient. However, the combination tested should not be interpreted as the only proportional combination covered by this invention. Although the testing was based on a 50/50 combination, reducing the dosage from 100% NTG NITROLINGUAL® Pumpspray (400 mcg/spray) to a dosage of 90% NTG NITROLINGUAL® Pumpspray (400 mcg/spray)/10% Menthol solution should also alleviate, to some degree, the side effects experienced by patients.

Further, menthol oils have a long lasting strong aromatic character. When this strong odor is coupled with the proven therapeutic effect of NTG, over time, the minimal effective NTG dosage may be reduced as a result of a learned conditioned reflex that the body associates with NTG. It is possible that over time, a patient may have the dosage of NTG reduced while the proportion of MCS is increased as the patient's body learns to associate MCS with the anti-anginal effect of NTG.

DETAILED DESCRIPTION

The following presents the results from two studies for using a mixture of NTG and 1% Menthol solution for treatment of anginal pain. The NTG used for the following tests was "NITROLINGUAL"® Pumpspray produced by Horizon Pharmaceutical Corporation, Rosewell, Ga. "Nitrolingual"® Pumpspray contains per single spray dosage 400 mcg NTG, an inactive amount of peppermint oil, and 20% alcohol.

First Study; First Test

The first study identifies 21 patients experiencing intolerance to a standard "Nitrolingual"® NTG 400 mcg spray dosage delivered sublingually. The NTG intolerance for 16 of the patients was in the form of prohibitive headaches while for 5 of the patients, it was fainting.

The "Nitrolingual"® solution described above was diluted fifty percent with a pharmacologically neutral solution placebo obtained from the same manufacturer, forming a combination solution. Both the placebo and the "Nitrolingual"® Pumpspray solutions exhibited the same density and viscosity so that fluid separation would not occur. Each of the patients was then provided with a pump spray containing the combination solution which would limit each single spray dosage to 200 mcg NTG.

Of the 21 patients studied, 90% (19 patients) did not experience intolerance. However, only 19% (4 patients) received satisfactory relief from anginal pain within two minutes following administration of a single 200 mcg NTG spray dosage. Therefore, undesirable side effects as well as relief from anginal pain were determined to be dose related.

First Study; Second Test

Next, isovolumic amounts of "Nitrolingual"® Pumpspray solution and 1% Menthol solution were mixed and the combination solution was provided to patients as a pump spray.

Of the 21 patients, none experienced an intolerance while all experienced anginal relief within two minutes after receiving a spray dosage containing 200 mcg NTG and an equivalent volumetric amount of 1% Menthol solution. The reduced delivery of NTG (200 mcg vs. 400 mcg) together with an equivalent volumetric amount of 1% Menthol solution, eliminated intolerance, but still provided relief from anginal pain as if a 400 mcg NTG spray dosage had been administered.

Second Study

The second study pertained to five patients that experienced reproducible exertional angina. The study comprised administering exercise stress tests for each patient on three consecutive days.

The following three tables illustrate the physical condition of each patient for stress testing when no NTG is administered (Table 1), 400 mcg NTG is administered (Table 2), and, 200 mcg NTG administered with an equivalent volumetric amount of 1% Menthol solution (Table 3).

For each patient, the stress test was stopped with the onset of angina. The objective evidence of ischemia was indicated by the degree of S-T segment depression and presence of segmental wall abnormalities documented by echocardiographic study performed immediately after the exercise stress test.

TABLE 1

NO NTG ADMINISTERED PRIOR TO EXERCISE

| Patient Number | Duration of Exercise in Minutes | Heart Rate at Peak |
| --- | --- | --- |
| 1 | 4 | 110 |
| 2 | 3.5 | 117 |
| 3 | 3.5 | 98 |
| 4 | 5 | 114 |
| 5 | 4 | 104 |

TABLE 2

400 mg NTG ADMINISTERED 5 MINUTES PRIOR TO EXERCISE

| Patient Number | Duration of Exercise in Minutes | Heart Rate at Peak |
| --- | --- | --- |
| 1 | 6 | 128 |
| 2 | 6.5 | 140 |
| 3 | 4.5 | 112 |
| 4 | 7.5 | 130 |
| 5 | 5 | 120 |

TABLE 3

200 mg NTG/1% Menthol ADMINISTERED 5 MINUTES PRIOR TO EXERCISE

| Patient Number | Duration of Exercise in Minutes | Heart Rate at Peak |
| --- | --- | --- |
| 1 | 6.5 | 130 |
| 2 | 6.5 | 144 |
| 3 | 4 | 110 |
| 4 | 8 | 130 |
| 5 | 6 | 128 |

All tests monitored angina with exercise, exercise tolerance, and the degree of S-T segment depression on the ECG, when: 1) no medication was administered (Table 1); 2) 400 mcg NTG spray alone was administered 3–4 minutes prior to exercise (Table 2); and, 3) a solution containing isovolumic amounts of NTG and Menthol solution in a pump spray for delivery of a 200 mcg NTG dosage was administered 3–4 minutes prior to exercise.

The test results shown in the above tables indicate that when NTG is used in half dose (200 mcg) in combination with menthol solution, the patient can perform essentially the same level of exercise as performed with a 400 mcg NTG spray dosage.

When 200 mcg NTG was used in combination with Menthol, or when 400 mcg NTG was administered by itself, the effect on exercise tolerance, S-T segment depression or time elapsed from the beginning of exercise to the onset of angina was essentially the same, despite the fact, that the amount of NTG used with Menthol was half. No side effects were observed in either group, but the desired medicinal effect was achieved.

Then NTG was used vs. NTG mixed with Menthol solution and Menthol/placebo solution without NTG. It was given to the first timers with angina (angina de novo) in a double blind study, since these patients are most sensitive to NTG. The patients, who complained of headaches the most, were those taking pure NTG without added Menthol.

I claim:

1. A method for treating a human experiencing anginal pain comprising the steps of:

providing an anti-anginal pain medication comprising substantially a 50-50 volumetric mixture of menthol solution to nitroglycerin solution where said mixture provides the same anginal pain relief as a solution consisting only of double the concentration of nitroglycerin as present in said 50-50 mixture; and, administering said 50-50 mixture sublingually.

2. A method for reducing over time the dosage of nitroglycerin administered to a patient suffering from anginal pain comprising the steps of:

providing a first anti-anginal pain medication comprising 100% nitroglycerin and 0% menthol containing substances for sublingual delivery as determined by the patient; and, under supervision of a treating physician, replacing said first anti-anginal pain medication with a second anti-anginal pain medication comprising a mixture (100−x)% nitroglycerin and (0+x)% menthol containing substances for sublingual delivery as determined by the patient, said second anti-anginal pain medication providing the same degree of relief from anginal pain as said first anti-anginal pain medication.

3. The method of claim 1 for treating a human experiencing anginal pain wherein said administering said mixture sublingually is by a pumpspray.

4. The method of claim 1 for treating a human experiencing anginal pain wherein said administering said mixture sublingually is by aerosol spray.

5. A method for reducing over time the dosage of nitroglycerin administered to a patient suffering from anginal pain comprising the steps of:

providing a first anti-anginal pain medication comprising 100% "NITROLINGUAL"® Pumpspray containing 400 mcg nitroglycerin and 0% additional menthol containing substances for sublingual delivery as determined by the patient; and, under supervision of a treating physician, replacing said first anti-anginal pain medication with a second anti-anginal pain medication comprising a volumetric proportion mixture of (100-x)% "NITROLINGUAL"® Pumpspray containing 400 mcg nitroglycerin and a solution comprising (0+x)% menthol containing substances for sublingual delivery as determined by the patient, said second anti-anginal pain medication providing substantially the same degree of relief from anginal pain as said first anti-anginal pain medication.

* * * * *